(12) United States Patent
Gregory et al.

(10) Patent No.: US 8,176,801 B2
(45) Date of Patent: May 15, 2012

(54) INTERFACE PORT FOR CONNECTION OF A SAMPLING DEVICE TO AN ANALYTICAL INSTRUMENT

(75) Inventors: Mark A. Gregory, Lafayette, IN (US); Jason L. Springston, Carmel, IN (US); Matthew Briscoe, Zionsville, IN (US); Garth E. Patterson, Brookston, IN (US); John W. Grossenbacher, Lafayette, IN (US); Dennis Barket, Jr., Lafayette, IN (US)

(73) Assignee: Griffin Analytical Technology, L.L.C., West Lafayette, IN (US)

( * ) Notice: Subject to any disclaimer, the term of this patent is extended or adjusted under 35 U.S.C. 154(b) by 626 days.

(21) Appl. No.: 12/003,312

(22) Filed: Dec. 21, 2007

(65) Prior Publication Data

US 2008/0163669 A1     Jul. 10, 2008

Related U.S. Application Data

(60) Provisional application No. 60/876,510, filed on Dec. 22, 2006.

(51) Int. Cl.
*G01N 1/00* (2006.01)
(52) U.S. Cl. .................................................... 73/864.81
(58) Field of Classification Search .................. None
See application file for complete search history.

(56) References Cited

U.S. PATENT DOCUMENTS

| | | | |
|---|---|---|---|
| 2,510,125 A * | 6/1950 | Meakin | 174/47 |
| 4,091,674 A | 5/1978 | Amey | |
| 4,170,901 A | 10/1979 | Conkle et al. | |
| 4,584,887 A | 4/1986 | Galen | |
| 4,718,268 A | 1/1988 | Reid et al. | |
| 5,124,274 A | 6/1992 | Ohki et al. | |
| 5,138,889 A | 8/1992 | Conrad | |
| 5,142,143 A | 8/1992 | Fite et al. | |
| 5,197,895 A * | 3/1993 | Stupecky | 439/194 |
| 5,336,467 A * | 8/1994 | Heidt et al. | 422/64 |
| 5,500,369 A | 3/1996 | Kiplinger | |
| 5,585,575 A | 12/1996 | Corrigan et al. | |
| 6,167,767 B1 | 1/2001 | Mengel et al. | |
| 6,230,573 B1 | 5/2001 | Schulten et al. | |
| 6,321,609 B1 | 11/2001 | Mengel et al. | |
| 6,446,514 B1 | 9/2002 | Danylewych-May et al. | |
| 6,477,906 B1 | 11/2002 | Peterson | |

(Continued)

FOREIGN PATENT DOCUMENTS

WO     WO-00/26405     5/2000

(Continued)

OTHER PUBLICATIONS

International Search Report for Application No. GB0811814.3 dated as searched on Oct. 21, 2008 (2 pages).

(Continued)

*Primary Examiner* — Robert R Raevis
(74) *Attorney, Agent, or Firm* — Wells St. John P.S.

(57) ABSTRACT

The present invention relates to devices for collecting and storing chemical samples and transferring those samples to analytical devices for analysis. In one implementation the device includes an interface for transferring samples and electrical signals. In another implementation, the device includes an analytical device having an interface for transferring samples and electrical signals with a sampling device. In another implementation, the device includes a sampling device having an interface for transferring samples and electrical signals with an analytical device.

23 Claims, 4 Drawing Sheets

U.S. PATENT DOCUMENTS

| | | | |
|---|---|---|---|
| 7,161,142 B1 | 1/2007 | Patterson et al. | |
| 2003/0236015 A1* | 12/2003 | Edirisuriya et al. | 439/191 |
| 2004/0123679 A1 | 7/2004 | Coleman et al. | |
| 2004/0224422 A1 | 11/2004 | Bonne et al. | |
| 2008/0229805 A1 | 9/2008 | Barket et al. | |

FOREIGN PATENT DOCUMENTS

| | | | |
|---|---|---|---|
| WO | WO-02/40964 A1 | | 5/2002 |
| WO | WO 2005/047865 | | 5/2005 |
| WO | WO 2005/078330 | * | 8/2005 |
| WO | WO 2005/103641 | | 11/2005 |
| WO | WO 2006/062906 | | 6/2006 |

OTHER PUBLICATIONS

English Translation of Office Action in Chinese Patent Application No. 200710093296.6 (3 pages).

V. Camel et al., Trace enrichment methods for the determination of organic pollutants in ambient air, Journal of Chromatography A, vol. 710, No. 1, pp. 3-19 (1995).

Markes International LTD., Chemical Warfare Agents & Homeland Security (2008), http://www.markes.com/en/ChemicalWarfare/default.aspx (last visited Mar. 11, 2008).

Teledyne Technologies, INC., Teledyne Tekmar Products (2006), http://www.teledynetekmar.com/products/index.asp (last visited Mar. 11, 2008).

CDS Analytical, INC., Dynatherm Chemical Agent Monitors Home Page (2004), http://www.cdsanalytical.com/dynatherm/dynatherm.html (last visited Mar. 11, 2008).

Inficon, Inficon Product Index, http://www.inficon.com/en/productindex.html (last visited Mar. 12, 2008).

Inficon, HAPSITE Chemical Identification System Brochure (2004), *available at* http://www.inficon.com/download/en/HAPSchemidentsys.pdf (last visited Mar. 12, 2008.

Inficon, HAPSITE Headspace Sampling System Brochure (2003), *available at* http://www.inficonchemicalidentificationsystem.com/en/pdf/HAPSITEheadspace.pdf (last visited Mar. 11, 2008).

Inficon, HAPSITE Accessory Catalog (2007), *available at* http://www.inficon.com/download/en/dild30a1%20HAPSITE%20Accessory%20Catalog.pdf (last visited Mar. 11, 2008).

Inficon, HAPSITE Situprobe Brochure (2007), *available at* http://www.inficon.com/download/en/situprobe.pdf (last visited Mar. 11, 2008).

Inficon, HAPSITE Smart Chemical Identification System Brochure (2004), *available at* http://www.inficon.com/download/en/haps-smart.pdf (last visited Mar. 11, 2008).

Inficon, HAPSITE Smart Plus Chemical Identification System Brochure (2007), *available at* http://www.inficon.com/download/en/HAPSITE_Smart_Plus_LR.pdf (last visited Mar. 11, 2008).

Inficon, HAPSITE VIPER Chemical Identification System with 267 Surface Sampler Brochure (2006), *available at* http://www.inficon.com/download/en/hapsitev.pdf (last visited Mar. 11, 2008).

Inficon, Scentograph CMS100 Brochure (2003), *available at* http://www.inficonchemicalmonitorinqsystems.corn/en/Scentographcms100.html (last visited Mar. 11, 2008).

Inficon, Scentograph CMS200 Brochure (2003), *available at* http://www.inficonchemicalmonitoringsystems.com/en/pdf/Scentograph_CMS200_Brochure.pdf (last visited Mar. 11, 2008).

Hi-Q Environmental Products Co., HVP-3800AFC & HVP-3500AFC Series Samplers Information page, *available at* http://store.hi-q.net/Item/Page3.htm (last visited Mar. 11, 2008).

Hi-Q Environmental Products Co., HVP-4200AFC & HVP-4300AFC Series Information page, *available at* http://store.hi-q.net/Item/HVP4200AFCHVP4300AFCSeries.htm (last visited Mar. 11, 2008).

Spectrex Corp., Operating Manual PAS-2000 Personal Air Sampler (Jun. 2003), *available at* http://www.spectrex.com/html_files/pdf/PAS-2000%20manual.pdf (last visited Mar. 11, 2008).

Spectrex Corp., Operating Manual PAS-500 Personal Air Sampler, *available at* http://www.spectrex.com/html_files/pdf/PAS500manual.pdf (last visited Mar. 11, 2008).

* cited by examiner

US 8,176,801 B2

INTERFACE PORT FOR CONNECTION OF A SAMPLING DEVICE TO AN ANALYTICAL INSTRUMENT

CROSS-REFERENCE TO RELATED APPLICATION

This application claims the benefit of U.S. Provisional Application No. 60/876,510, filed Dec. 22, 2006, by Mark Gregory, Jason Springston, Matthew Briscoe, Garth Patterson, John Grossenbacher, and Dennis Barket and titled INTERFACE PORT FOR CONNECTION OF A SAMPLING DEVICE TO AN ANALYTICAL INSTRUMENT, the disclosure of which is expressly incorporated herein by reference.

GOVERNMENT RIGHTS

This invention was made with Government support under SBIR Phase III Contract M67004-04-C-0014 awarded by the United States Marine Corps. The Government has certain rights in the invention.

FIELD OF THE INVENTION

The present invention relates to devices for collecting and storing chemical samples and transferring those samples to analytical devices for analysis.

BACKGROUND OF THE INVENTION

Various devices are known in the art for chemically analyzing samples. For example, devices such as mass spectrometers, flame ionization detectors, gas-chromatographs, combination gas-chromatographs/mass spectrometers or gas-chromatographs/flame ionization detectors are all known devices for analyzing chemical samples. Historically, these devices have been of large size and restricted to use only in a laboratory environment. Moreover, in the past, the ability to obtain samples for analysis by these devices at locations away from the analysis device has been limited.

Presently, however, there is an increasing demand for smaller, hand-held sample collection devices that are capable of obtaining samples in the field, properly storing those samples, and then transferring those samples to an appropriate analysis device that is either also located in the field or is located in a fixed laboratory. The use of a hand-held sampler extends the analytical capabilities of the analysis system that, for particular reasons, may not be located at the area in which the sample resides. These samplers must be capable of not only storing the samples, but transferring those samples to an analysis system. One example of such a portable sample collection system is described in the pending PCT Patent Application Publication No. WO 2006/062906, which is hereby expressly incorporated herein by reference.

Embodiments of the present invention provide for an improved interface between a sampler and an analytical device.

SUMMARY OF THE INVENTION

Apparatus consistent with one embodiment of the invention provides an interface for connecting a sampling system and an analysis system. The interface includes a male component having a protruding portion and a male connector attached to the protruding portion including at least one fluid connector and at least one electrical connector. The interface also includes a female component having a cavity designed to mate with the protruding portion of the male component such that the male component can only be inserted in the cavity with one specified orientation and a female connector located in the cavity designed to mate with the at least one fluid connector and at least one electrical connector of the male component. The male component and female component are configured so that when they are mated fluid may pass between the male component and the female component and electrical signals may be sent between the connected female and male components.

Apparatus consistent with another embodiment of the invention provides an analysis system. The analysis system includes a chemical analyzer and an interface located on the chemical analyzer. The interface has a cavity designed to mate with a protruding portion of a component of a sampling system such that the component of the sampling system can only be inserted in the cavity with one specified orientation and a female connector located in the cavity designed to mate with at least one fluid connector and at least one electrical connector of the sampling system.

Apparatus consistent with another embodiment of the invention provides a sampling system. The sampling system includes a sample collector and an interface located on the sample collector. The interface has a protruding portion and a male connector attached to the protruding portion including at least one fluid connector and at least one electrical connector, wherein the protruding portion is designed to mate with a cavity in only one orientation.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one embodiment of the invention and together with the description, serve to explain the principles of the invention.

DESCRIPTION OF THE EMBODIMENTS

Reference will now be made in detail to the exemplary embodiments of the invention, an example of which is illustrated in the accompanying drawings. Wherever possible, the same reference numbers will be used throughout the drawings to refer to the same or like parts.

Figure 2A:
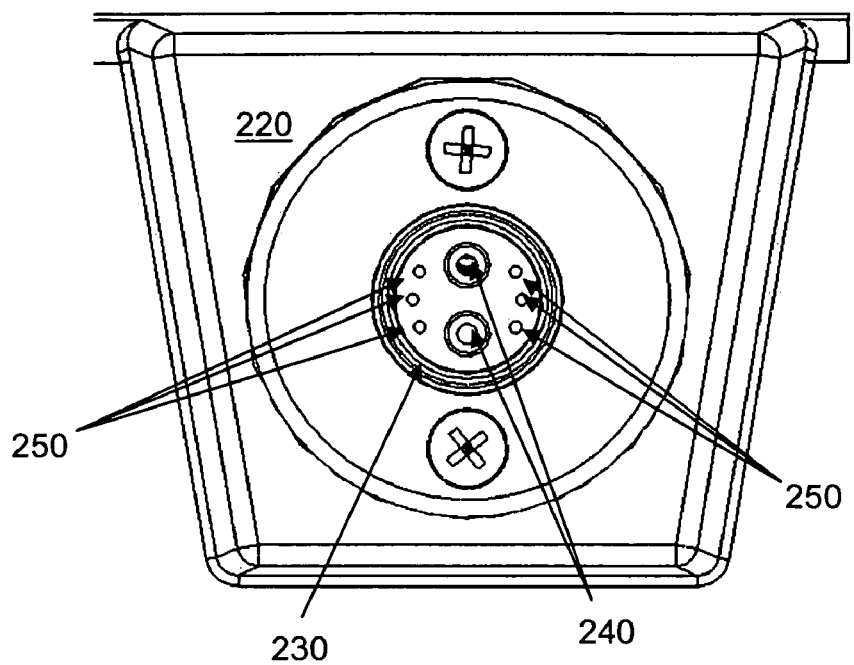
FIG. 2A is a front view of a male component of an interface on a sampling system consistent with one embodiment of the invention.
Figure 2B:
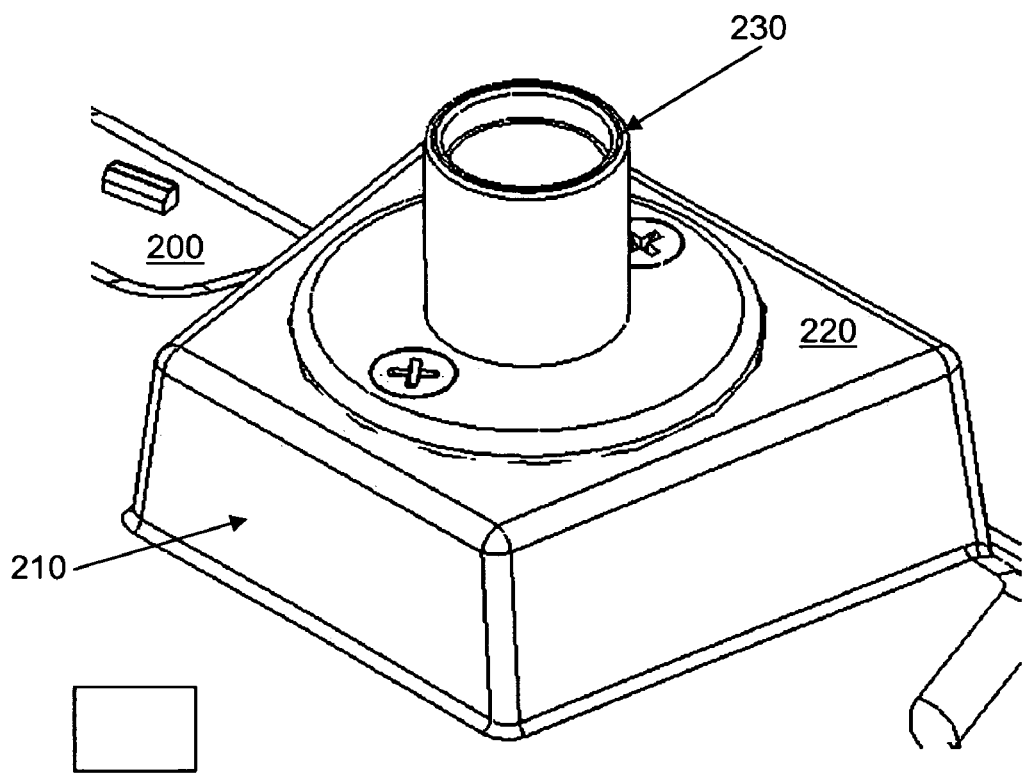
FIG. 2B is a perspective view of the male component depicted in FIG. 2A.
Figure 3:
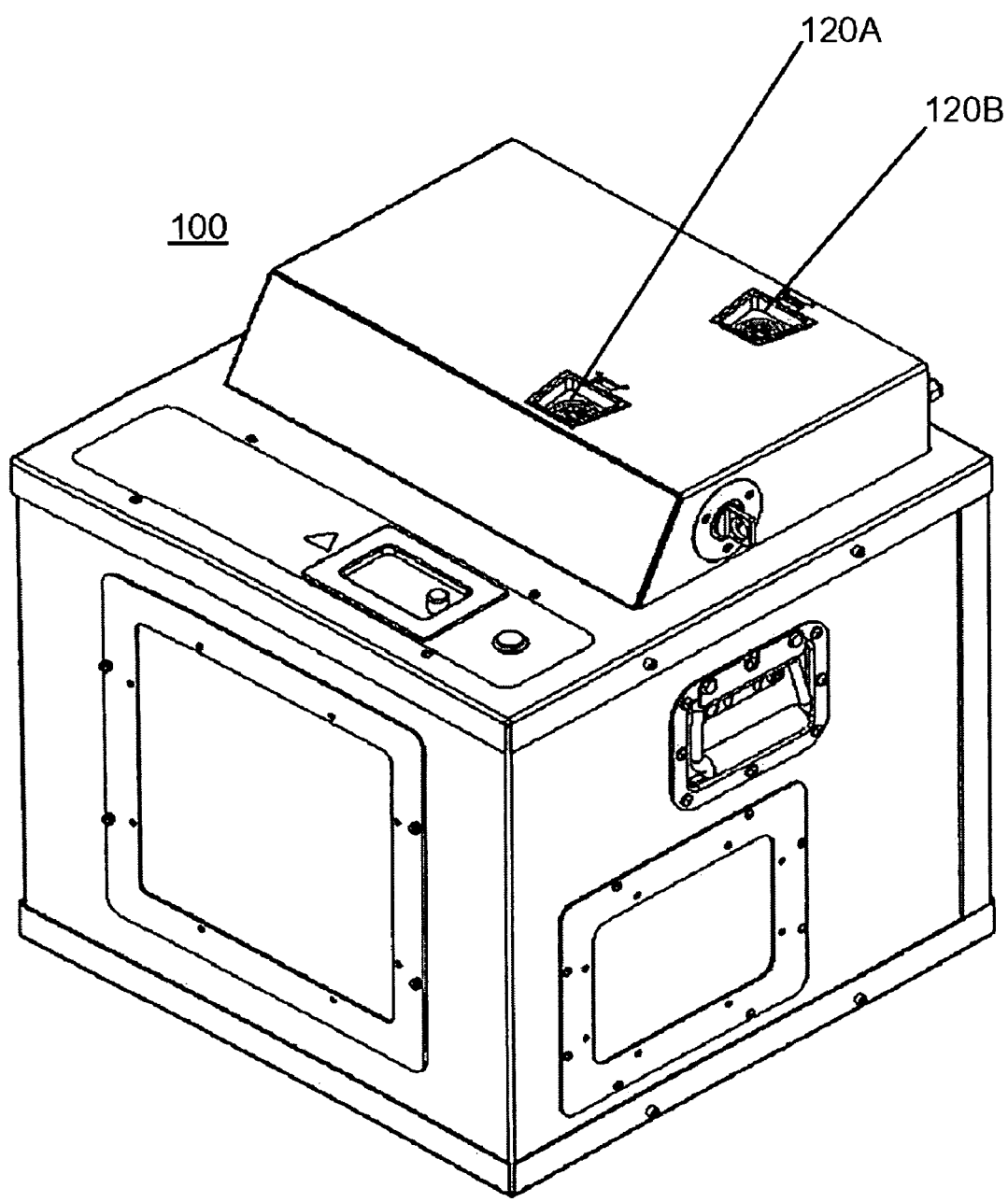
FIG. 3 is a perspective view of an analysis system including a female component of an interface, consistent with one embodiment of the invention.
Figure 4:
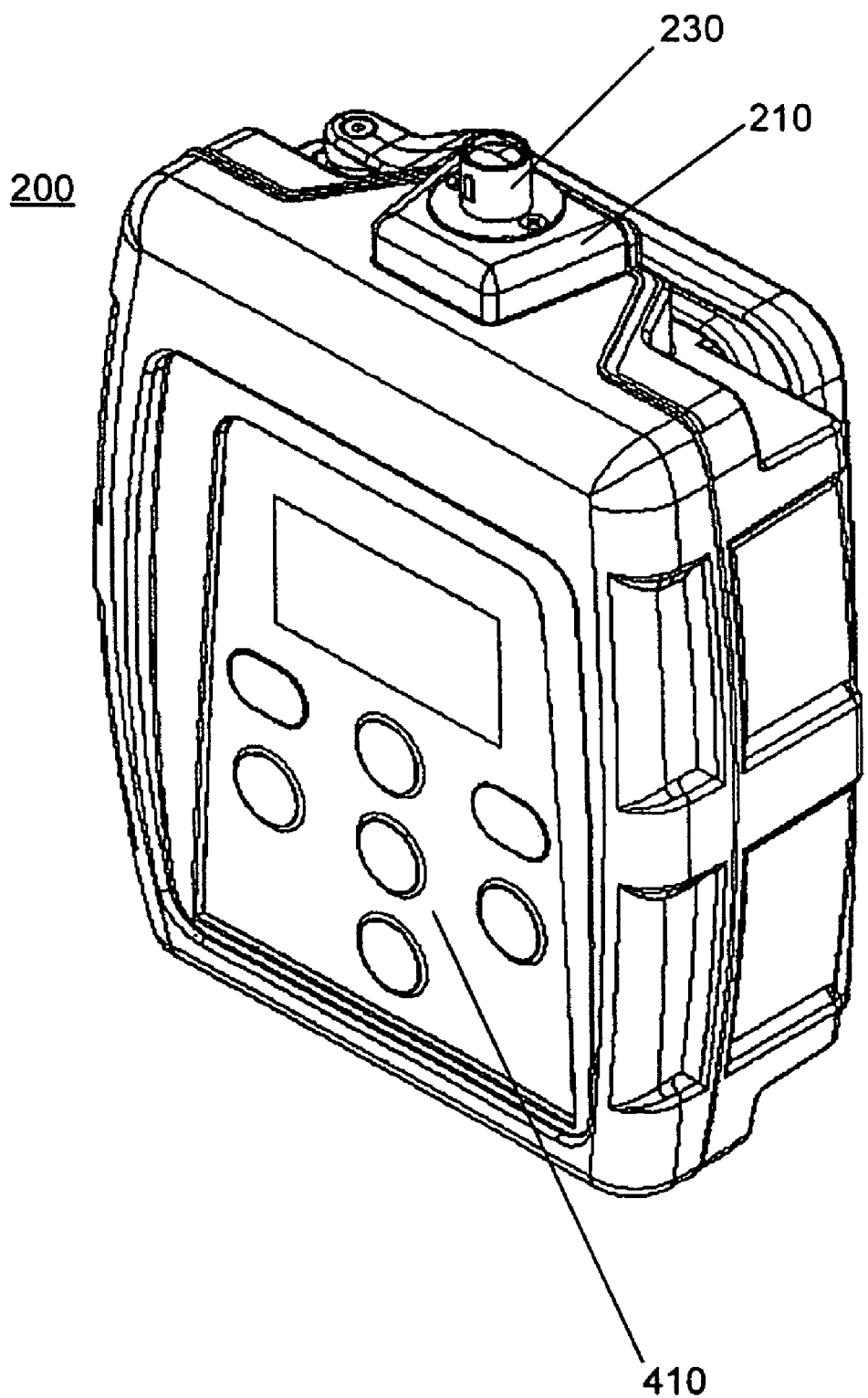
FIG. 4 is a perspective view of a sampling system including a male component of an interface, consistent with one embodiment of the invention.

As explained above, an external sampling system may be used to obtain a sample to be analyzed. FIG. 4 illustrates one example of a sampling system 200 consistent with one embodiment of the invention. Once the sample is collected, the sampling system may be connected with an analysis system to allow for extraction of the collected sample components followed by detection of the chemical species present. FIG. 3 illustrates one example of an analysis system 100 consistent with one embodiment of the invention. The interface of the present invention provides a convenient means of attaching a sampling system, such as sampling system 200 to an analysis system, such as analysis system 100. In one embodiment, as illustrated in FIGS. 2A-2B and 4, the sampling system 200 may be a hand-held sample collector. The interface of the invention is not limited to hand-held sample collectors, however, and could be used to connect sampling systems of various sizes and configurations, such as portable but not hand-held samplers, or non-portable devices. Moreover, as explained below, in one embodiment, the interface allows an analytical system to support a variety of sample introduction devices in order to maintain flexibility of sample collection and transfer.

Figure 1A:
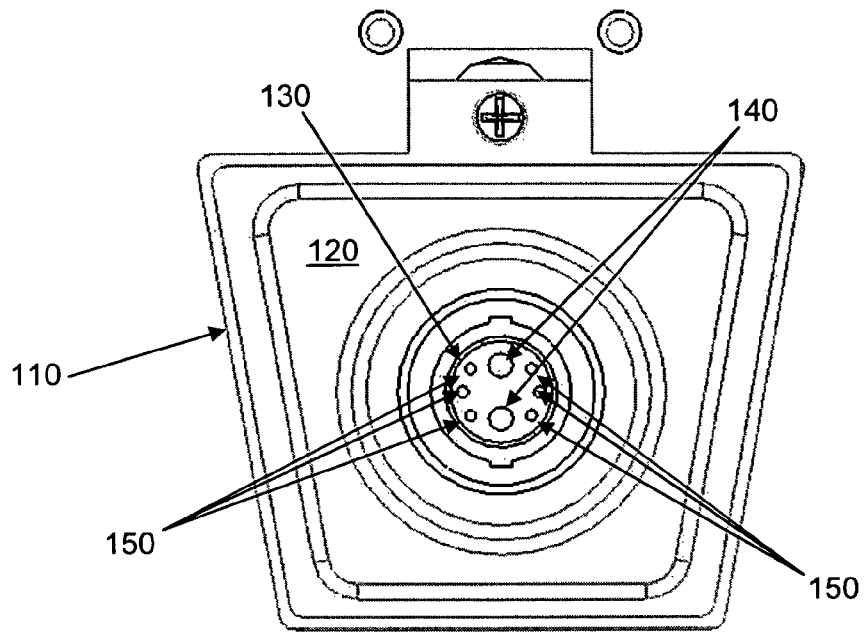
FIG. 1A is a front view of a female component of an interface on an analysis system consistent with one embodiment of the invention.

FIGS. 1A-4 depict an interface for connecting a sampling system to an analysis system consistent with one embodiment of the invention. The interface may consist of two components: a "female" component 120 and a "male" component 210. The interface allows for a connection when the male component is inserted into the female component such that the male component "nests" inside the female component. In the embodiment depicted in FIGS. 1A-2B, the female component 110 is located on the analysis system 100 (as depicted in FIGS. 1A, 1B, and 3) and the male component 210 is located on the sampling system 200 (as depicted in FIGS. 2A, 2B, and 4). It should be understood, however, that the male component could be located on the analysis system and the female component could be located on the sampling system.

Figure 1B:
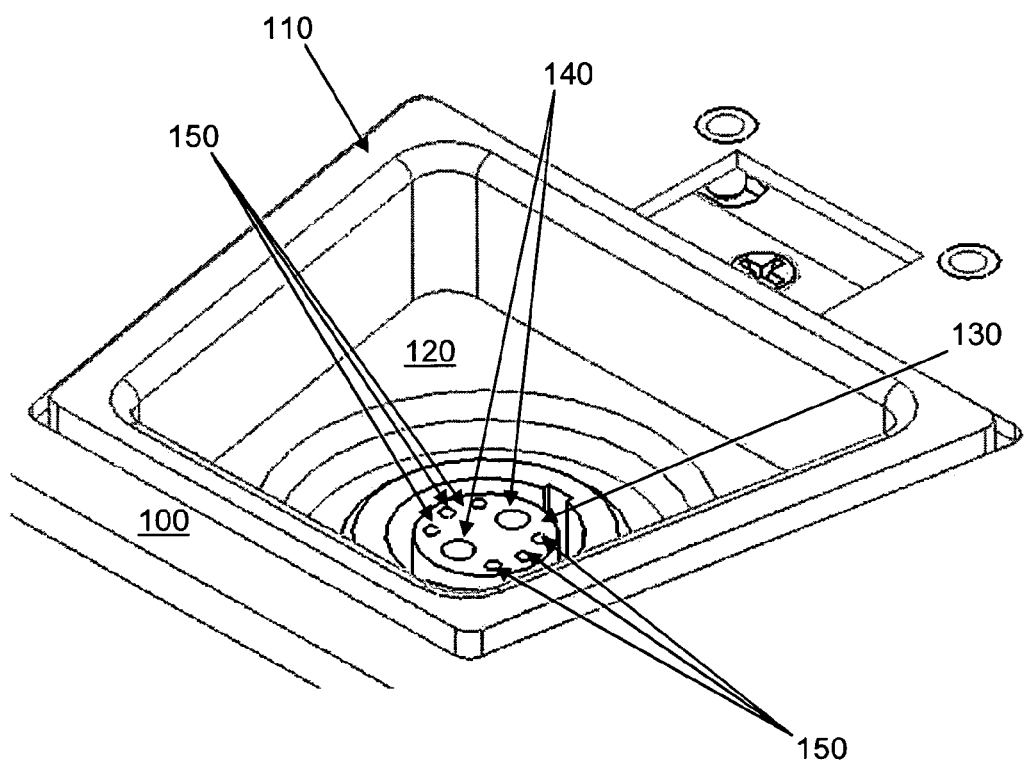
FIG. 1B is a perspective view of the female component depicted in FIG. 1A.

As shown in FIGS. 2A-2B, the male component 210 of the interface includes a trapezoidal protrusion 220 and a connector 230 attached to the trapezoidal protrusion. As shown in FIG. 2B, connector 230 is attached to the trapezoidal protrusion 220 with screws, however, any suitable attachment means could be used. Correspondingly, as shown in FIGS. 1A-1B, the female component 110 has a connector 130 located within a trapezoidal cavity 120. The trapezoidal protrusion 220 and connector 230 are designed to mate with the trapezoidal cavity 120 and connector 130 when the male component 210 is inserted into the female component 110.

One feature of the trapezoidal protrusion 220 and the trapezoidal cavity is that it allows the components 110 and 210 of the interface to be connected in only one orientation. This ensures proper operation without electrical or mechanical damage. While FIGS. 1A-2B depict a trapezoidal protrusion other shapes that provide for only one orientation may also be used consistent with the invention. For example, a trapezoid having sides of different lengths than that shown in FIGS. 1A-2B could be used. The invention in its broadest sense is not limited to particular shapes. For example, while the protrusions are described for exemplary purposes as being trapezoidal, any shape can be used consistent with the invention. For example, protrusions having cross-sections with more than four sides could be used, such as a pentagon, hexagon, or octagon. In a preferred embodiment, the shape should provide for only one correct orientation. However, if the systems is designed to work with multiple orientations, then shapes permitting multiple orientations may be used, such as a circular or triangular protrusion. Similarly other structural details may be employed to ensure correct orientation. Similarly, more irregular shapes could also be used.

Connectors 130 and 230 include the fluid and/or electrical interfaces that provide the fluid and/or electrical connections between the sampling system and the analytical system. Connectors 130 include fluid connections 140 and 240 and electrical connections 150 and 250. In the embodiment of FIGS. 1A-2B, there are two fluid connections on each component and six electrical connections. Any number of suitable fluid and electrical connections, however, could be used in the interface of the invention.

As shown in FIGS. 1A-2B, connectors 130 and 230 are designed so that when mated, the cylindrical exterior wall of connector 230 will be positioned around the cylindrical exterior wall of connector 130. The invention in its broadest sense is not limited to particular shapes for connectors 130 and 230. For example, while the male and female connectors 130 and 230 illustrated are cylindrical, any mating shapes could be used consistent with the invention. When mated, fluid connections 240 will nest inside fluid connections 140 and electrical connections 150 will nest inside electrical connections 250. While the nesting feature is one exemplary aspect of the invention, the invention is not limited to embodiments where all of the connections nest. Fluid connections 140 and 240 and electrical connections 150 and 250 may be any standard fluid connectors and electrical connectors used to transfer fluids and electrical signals, respectively. For example, electrical connectors, including, but not limited to, power connectors, RS-232 devices, USB connectors, 8P8C connectors, or firewire connectors may be used.

As illustrated in the exemplary embodiment, the interface provides secure, mechanical stabilization for the connected device to maintain a stable, protected connection. The interface on this embodiment allows for conduction of fluids, i.e. gases or liquids depending on the sampling scenario, bidirectionally to and/or from the sampling system 200. The fluid flow may be driven by pumping means internal or external to the analysis instrument. Similarly, the fluid may be provided from a fluid source internal or external to the analysis instrument. The fluid flow may also include the introduction of a carrier gas from the analysis system 100 to the sampling system 200.

The electrical connections 150 and 250 may allow for electrical power or signals to be provided to components external to the analysis system 100 that may be used during sample transfer from the sampling system 200. These signals may be analog, digital, or both. These connections may also allow for electrical power and/or control signals to be provided to components external to the analysis system that may be used during sample transfer from the sampling system including, for example, heaters, valves, digital signal processors (DSPs), user interface controls 410 such as buttons and switches and status/diagnostic indicators or displays, as depicted in part in FIG. 4. The electrical power connections may also be used to charge a battery in a sampling system. In one implementation, two of the electrical connections are used for power supply and four connections are RS-232 connections. The external modules may be controlled by the analysis system 100 or, in some cases, directly with the interface 410 on the external system. If used with the invention, this control from one common point allows synchronization of the combined analytical system. These electrical signals may also provide digital information to the analysis system such as information about the collected sample. Such information can include, sample volume, sample collection time and date, sample ID, and sample location information via a Global Positioning System (GPS).

Depending on the intended application, an interface in accordance with the invention may support a variety of sample introduction means including, but not limited to: (1) an external, removable sample collection system 200; (2) an extended sample transfer line for direct fluid (gas or liquid) sampling or acceptance of samples from another system with its own user interface (purge and trap, preconcentrator, thermal desorber, or head-space systems); (3) a selectively-permeable membrane-equipped probe where the membrane barrier is situated within the probe or located integrally to the analysis system; (4) a sample probe for interfacing to gas- or liquid-handling systems found in at-line or near-line process monitoring applications; and (5) a sample introduction system employing an integrated solvent rinse or thermal release technique to obtain a sample from a surface such as a solid-phase microextraction (SPME) inlet to obtain a sample from a surface or in the absence of a module connected to the interface, a simplified sample inlet port. The system may also support a sample generator that generates a chemical sample internally for later analysis.

In addition, the analysis system may be equipped with one or more interfaces 120, as depicted in FIG. 3. One such interface may be considered the main interface 120A and may be the only one so configured to accept analytical samples transferred from the hand-held sample collector or other inlet as described above. The analytical system can be equipped with one or a plurality of additional, secondary interfaces 120B. These connections can allow electrical signals and gas flow to connected devices in order to allow cleaning of the connected sample collector or other inlet device described above. In this case, fluid (typically inert, i.e. oxygen- or other oxidant-free gas) and electrical signals are provided to flush residual chemical signatures or possible contaminants from the sampling system resulting in a cleaner collection or inlet system.

Embodiments consistent with the invention may use the interface in any number of settings for sample collection, transfer, or analysis. For example, in one exemplary embodiment, the male component of the interface may be located on a hand-held sampler for use in detection of chemical weapons. The sampler would be used to collect a sample in the field. It would then be connected to an gas chromatograph/mass spectrometer (GC/MS) via the interface. The interface would transfer the sample to the GC/MS via the fluid connections. This transfer may be initiated via the electrical connections between the sampler and the analysis system. Upon successful transfer of the sample, the sampler would be connected to a secondary interface on the GC/MS to flush out any remaining chemical residues. This embodiment is merely exemplary and many other uses are contemplated. For example the interface could be used with samplers to detect chemical warfare agents, explosives, toxic industrial chemicals, or other pollutants. In addition, the interface could be used to transfer samples to mass spectrometers, flame ionization detectors, gas-chromatographs, combination gas-chromatographs/mass spectrometers, gas-chromatographs/flame ionization detectors, surface acoustic wave systems, ion mobility spectrometer systems, or any other devices or combination of devices for analyzing chemical samples.

While the above described interface has been depicted as utilizing a sample collector and an analyzer, the invention is not intended to be limited to this particular structure. Therefore, sample introducing alternatives to sample collectors are intended to be within the scope of this invention. Furthermore, suitable known analyzers are intended to be within the scope of this invention, including mass spectrometers and chromatographs. Additionally, it is contemplated that individual features of one embodiment may be added to, or substituted for, individual features of another embodiment. Accordingly, it is within the scope of this disclosure to cover embodiments resulting from substitution and replacement of different features between different embodiments.

The above described embodiments and arrangements are intended only to be exemplary of contemplated interfaces. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An interface for connecting a sampling system and an analysis system comprising:
    a male component having:
        a protruding portion with a trapezoidal cross-section; and
        a male connector attached to the protruding portion including at least one fluid connector and at least one electrical connector; and
    a female component having:
        a cavity designed to mate with the protruding portion of the male component such that the male component can only be inserted in the cavity with one specified orientation; and
        a female connector located in the cavity designed to mate with the at least one fluid connector and at least one electrical connector of the male component;
    wherein the male component and female component are configured so that when they are mated fluid may pass between the male component and the female component and electrical signals may be sent between the connected female and male components.

2. The interface of claim 1, wherein the male component is part of a sampling system and the female component is part of an analysis system.

3. The interface of claim 2, wherein the sampling system comprises a user interface.

4. The interface of claim 2, wherein the analysis system is a gas chromatograph and/or mass spectrometer.

5. The interface of claim 2, wherein the electrical connectors provide information about a sample from the sampling system to the analysis system.

6. The interface of claim 5, wherein the sample information includes at least one of the sample volume, sample collection time, sample collection date, or sample collection location.

7. The interface of claim 1, further comprising a pump configured to facilitate fluid transfer between the sampling system and the analysis system.

8. The interface of claim 1, wherein fluid may pass in either direction between the male component and female component.

9. An analysis system comprising:
    a chemical analyzer; and
    an interface located on the chemical analyzer, the interface having:
        a cavity designed to mate with a protruding portion of a component of a sampling system such that the component of the sampling system can only be inserted in the cavity with one specified orientation; and
        a female connector located in the cavity designed to mate with at least one fluid connector and at least one electrical connector of the sampling system.

10. The analysis system of claim 9, wherein the chemical analyzer includes:
> a second interface located on the chemical analyzer, the second interface comprising:
>> a cavity designed to mate with the protruding portion of the component of the sampling system such that the component of the sampling system can only be inserted in the cavity with one specified orientation; and
>> a female connector located in the cavity designed to mate with at least one fluid connector and at least one electrical connector of the sampling system.

11. The analysis system of claim 10, wherein the second interface is configured to allow the analysis system to flush out at least part of the sampling system.

12. The analysis system of claim 9, wherein the analysis system is a gas chromatograph and/or mass spectrometer.

13. The analysis system of claim 9, wherein fluid may pass in either direction between the analysis system and the sampling system.

14. A sampling system comprising:
> a sample collector; and
> an interface located on the sample collector, the interface having:
>> a protruding portion; and
>> a male connector attached to the protruding portion including at least one fluid connector and at least one electrical connector;
> wherein the protruding portion is designed to mate with a cavity at only one orientation.

15. The sampling system of claim 14, wherein the sample collector is hand-held.

16. The sampling system of claim 14, wherein the sample collector comprises a user interface.

17. A sampling and analysis system comprising:
> a sampling system comprising:
>> a male component having:
>>> a protruding portion; and
>>> a male connector attached to the protruding portion including at least one fluid connector and at least one electrical connector; and
> an analysis system comprising:
>> a female component having:
>>> a cavity designed to mate with the protruding portion of the male component such that the male component can only be inserted in the cavity with one specified orientation; and
>>> a female connector located in the cavity designed to mate with the at least one fluid connector and at least one electrical connector of the male component;
> wherein the male component and female component are configured so that when they are mated fluid may pass in either direction between the male component and the female component and electrical signals may be sent between the connected female and male components.

18. The sampling and analysis system of claim 17, wherein the analysis system is a gas chromatograph and/or mass spectrometer.

19. The sampling and analysis system of claim 17, wherein the sampling system is a handheld sampler.

20. A sampling and analysis system comprising:
> a sampling system; and
> an analysis system;
> wherein the sampling system comprises:
>> a sampling system interface configured to connect to the analysis system, the sampling system interface comprising;
>>> an electrical interface configured to electrically connect the sampling system to the analysis system; and
>>> a fluid interface configured to transfer fluid between the sampling system and the analysis system;
>> wherein the position of the fluid interface is fixed relative to the electrical interface prior to connection with the analysis system; and
> wherein the analysis system comprises:
>> an analysis system interface configured to connect to the sampling system, the analysis system interface comprising;
>>> an electrical interface configured to electrically connect the analysis system to the sampling system; and
>>> a fluid interface configured to transfer fluid between the analysis system and the sampling system; and
> wherein the sampling system interface is configured to mate with the analysis system interface at only one specified orientation.

21. A method of transferring a sample to an analyzer, comprising:
> providing a sample collector having an interface, the interface comprising at least one fluid connector and at least one electrical connector, the at least one fluid connector and at least one electrical connector configured to have a fixed position relative to each other prior to connection with an analyzer;
> providing an analyzer having an interface configured to mate with the interface of the sample collector in only one possible orientation;
> collecting a sample in the sample collector;
> connecting the sample collector to the analyzer;
> transferring electrical signals between the sample collector and the analyzer; and
> transferring the sample from the sample collector to the analyzer.

22. The method of claim 21, further comprising;
> providing a second interface on the analyzer;
> connecting the sample collector to the second interface after transferring the sample; and
> flushing out the sample collector through the second interface.

23. A sampling system comprising:
> a sample generator; and
> an interface located on the sample generator, the interface having:
>> a protruding portion; and
>> a male connector attached to the protruding portion including at least one fluid connector and at least one electrical connector;
> wherein the protruding portion is designed to mate with a cavity at only one orientation.

* * * * *